US009358337B2

(12) United States Patent
Dittrich

(10) Patent No.: US 9,358,337 B2
(45) Date of Patent: Jun. 7, 2016

(54) CHECK VALVE ARRANGEMENT

(75) Inventor: Marcus-Meinolf Dittrich, Frankfurt am Main (DE)

(73) Assignee: SANOFI - AVENTIS DEUTSCHLAND GMBH, Frankfurt am Main ( * ) Notice: Subject to any disclaimer, the term of this patent is extended or adjusted under 35 U.S.C. 154(b) by 36 days.

(21) Appl. No.: 14/119,209

(22) PCT Filed: May 23, 2012

(86) PCT No.: PCT/EP2012/059623

§ 371 (c)(1), (2), (4) Date: Nov. 21, 2013

(87) PCT Pub. No.: WO2012/160104

PCT Pub. Date: Nov. 29, 2012

(65) Prior Publication Data

US 2014/0188050 A1 Jul. 3, 2014

(30) Foreign Application Priority Data

May 24, 2011 (EP) .................................... 11167354

(51) Int. Cl.

*A61M 5/19* (2006.01)
*A61M 5/20* (2006.01)

(Continued)

(52) U.S. Cl.

CPC . *A61M 5/19* (2013.01); *A61M 5/20* (2013.01); *A61M 5/31546* (2013.01);

(Continued)

(58) Field of Classification Search

CPC .................. A61M 5/1408; A61M 2005/3128; A61M 39/22; A61M 39/24; A61M 39/26; A61M 5/19; A61M 2039/2473; A61M 2039/2433; A61M 2039/248; A61M 5/2066; A61M 5/16827; F16K 15/044

See application file for complete search history.

(56) References Cited

U.S. PATENT DOCUMENTS 3,771,556 A * 11/1973 Gifford .................... 137/533.11
4,898,204 A * 2/1990 Wallace ............. G05D 16/0658 137/505.41

(Continued)

FOREIGN PATENT DOCUMENTS

DE 9112950 U1 * 11/1991
EP 0110289 5/1986

(Continued)

OTHER PUBLICATIONS

International Search Report for Int. App. No. PCT/EP2012/059623, completed Nov. 26, 2012.
Chinese Office Action for CN App. No. 201280036388.X, issued Feb. 5, 2016.
Chinese Search Report for CN App. No. 201280036388.X, dated Jan. 28, 2016.
Japanese Office Action for JP App. No. 2014-511858, mailed Feb. 23, 2016.

*Primary Examiner* — Kami A Bosworth
*Assistant Examiner* — Nilay Shah
(74) *Attorney, Agent, or Firm* — McDonnell Boehnen Hulbert & Berghoff LLP

(57) ABSTRACT

The invention is related to an apparatus comprising a valve body comprising at least two inlet channels and at least one outlet channel and forming a central cavity connecting the at least two inlet channels and the at least one outlet channel, wherein the central cavity encloses a blocking assembly arranged for closing each of the at least two inlet channels by default and for opening an inlet channel when fluid pressure is applied from that inlet channel; wherein each of the at least two inlet channels is configured for fluid communication with a respective reservoir of at least two reservoirs. The invention is further related to a medical device for delivering at least two drug agents from at least two separate reservoirs comprising an apparatus of the aforementioned kind.

5 Claims, 13 Drawing Sheets

322 308
302 304
306

(51) Int. Cl.

| | |
|---|---|
| *F16K 15/04* | (2006.01) |
| *A61M 39/24* | (2006.01) |
| *A61M 39/26* | (2006.01) |
| *A61M 39/22* | (2006.01) |
| *A61M 5/315* | (2006.01) |
| *A61M 5/34* | (2006.01) |
| *A61M 5/24* | (2006.01) |
| *A61M 5/31* | (2006.01) |

(52) U.S. Cl.

CPC .............. *A61M 5/345* (2013.01); *A61M 39/22* (2013.01); *A61M 39/24* (2013.01); *A61M 39/26* (2013.01); *A61M 2005/2407* (2013.01); *A61M 2005/2474* (2013.01); *A61M 2005/2496* (2013.01); *A61M 2005/3128* (2013.01); *A61M 2039/248* (2013.01); *F16K 15/044* (2013.01); *Y10T 137/87684* (2015.04)

(56) References Cited

U.S. PATENT DOCUMENTS

| | | | | |
|---|---|---|---|---|
| 6,083,202 | A * | 7/2000 | Smith | 604/164.01 |
| 6,189,517 | B1 | 2/2001 | McCandless | |
| 2004/0143153 | A1 | 7/2004 | Sharrow | |
| 2004/0254542 | A1 | 12/2004 | Sacco | |

FOREIGN PATENT DOCUMENTS

| | | |
|---|---|---|
| EP | 0710487 | 5/1996 |
| EP | 2283885 | 2/2011 |
| JP | S59-113377 | 6/1984 |
| JP | -110-511014 | 10/1998 |
| JP | 2000-035146 | 2/2000 |
| JP | 2010-503464 | 2/2010 |
| WO | 96/14097 | 5/1996 |
| WO | 2008/036462 | 3/2008 |

* cited by examiner

CHECK VALVE ARRANGEMENT

CROSS REFERENCE TO RELATED APPLICATIONS

The present application is a U.S. National Phase Application pursuant to 35 U.S.C. §371 of International Application No. PCT/EP2012/059623 filed May 23, 2012, which claims priority to European Patent Application No. 11167354.7 filed May 24, 2011. The entire disclosure contents of these applications are herewith incorporated by reference into the present application.

TECHNICAL FIELD

The present patent application relates to medical devices of delivering at least two drug agents from separate reservoirs. Such drug agents may comprise a first and a second medicament. The medical device includes a dose setting mechanism for delivering the drug automatically or manually by the user. In particular, the present invention relates to a check valve arrangement as for example usable in such a medical drug delivery device.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

Because two or more different liquid drug components may pass through the body of the valve during the process of injection at different times, there is a risk that during the passing of a first drug component the reservoir of another drug component is contaminated by a reverse flow of the first drug component into the reservoir of the other component. This risk is particularly acute if and when the injection needle, and consequently also the outlet of the dispense interface, is blocked.

In some conventional valves which are constructed so as to block either one of two inlet channels, the effective blocking of a first inlet channel may depend on ongoing fluid flow from a second inlet channel into the valve's central cavity and out to the outlet channel. When the outlet channel is blocked and consequently fluid flow from the second inlet channel stops, the blocking mechanism may arrive in an equilibrium position in which neither inlet channel is effectively blocked, consequently resulting in possible fluid flow from the central cavity into the first inlet channel and contamination of the reservoir corresponding to the first inlet channel.

To prevent this from happening, additional precautions against any flow of the drug component to be currently injected from the dispense interface into any of the reservoirs of the other drug components are appropriate.

Thus it is an object of the invention to provide a valve arrangement for the dispense interface which eliminates or minimizes the possibility of a drug component flowing from a first reservoir and contaminating the reservoir of another drug component, especially for the situation in which the output needle of the injection device is blocked.

This object is solved by an apparatus comprising: a valve body comprising at least two inlet channels and at least one outlet channel and forming a central cavity connecting the at least two inlet channels and the at least one outlet channel, wherein the central cavity encloses a blocking assembly arranged for closing each of the at least two inlet channels by default and for opening an inlet channel when fluid pressure is applied from that inlet channel, wherein each of the at least two inlet channels is configured for fluid communication with a respective reservoir of at least two reservoirs.

This valve arrangement acts as a check valve. The blocking assembly closes each inlet channel by mechanically blocking the respective inlet channel. The blocking assembly may comprise blocking means. By having all inlet channels be closed by default, this valve arrangement ensures that liquid from a first reservoir entering the central cavity through one of the inlet channels does not flow into another reservoir through one of the other inlet channels. This holds true even when the outlet channel is directly or indirectly obstructed and the liquid from the first reservoir cannot escape through the outlet channel. The effective blocking of any inlet channel does not depend on ongoing flow from another inlet channel to the outlet channel but is always ensured as long as there is no fluid pressure from inside the respective blocked inlet channel. Thus the blocking of the inlet channel corresponding to the drug component that is currently not supposed to be delivered through the outlet channel occurs even when the needle is blocked and contamination of the reservoirs is avoided.

This valve arrangement may have any number of inlet channels and outlet channels. Each inlet channel may receive a fluid such as a drug component from a respective reservoir. The fluid may then be disposed through an injection mechanism connected to the outlet channel or outlet channels. At any given time, only fluid from one of the inlet channels is supposed to be flowing from that inlet channel into the central cavity and out through the outlet channel. The central cavity of the valve body houses an assembly configured for closing each of the inlet channels by default. This is done by mechanically blocking each inlet channel. That is, in the absence of fluid pressure from any of the inlet channels, each of the inlet channels is mechanically blocked such that no liquid can enter into any inlet channel from the central cavity. Therefore the opening of any inlet channel is not a prerequisite condition for the closing of the other inlet channels. However, the opening of any inlet channel may further reinforce the closing of the other inlet channels. The blocking mechanism is further arranged such that increasing pressure within the central cavity corresponds to boosted closing pressure on each of the inlet channels.

When a liquid such as a drug component flows from an inlet channel to the central cavity, the raised pressure from inside the inlet channel causes the blocking mechanism to open that inlet channel. The other inlet channels remain blocked and thus closed, thereby preventing liquid flow from the other inlet channels into the central cavity as well as from the central cavity into the other inlet channels. The liquid from the open inlet channel can then flow into the central cavity and out through the outlet channel. Once the flow from the reservoir via the inlet channel stops, pressure equilibrium between the central cavity and that inlet channel is restored and the blocking mechanism returns to blocking that inlet channel. But even if the liquid from the inlet channel cannot flow through the outlet channel, for example because of an accidental block in the outlet channel itself or in a needle attached to the outlet channel, flow into the other inlet channels is prevented because of the ongoing block of the other inlet channels. Thereby mixing of the liquids from the individual reservoirs and the according contamination is avoided.

A preferred embodiment is characterized in that the blocking assembly is configured to apply bias pressure on the at least two inlet channels. Thus the blocking assembly has geometric and material properties ensuring that by default, i.e. in the absence of any fluid pressure from any of the inlet channels or the outlet channels, the blocking assembly exerts pressure on all of the inlet openings acting to close the inlet openings. This can be achieved for example by using a deformable object as a blocking assembly, which deformable object is fit into the central cavity under strain. By straining to expand, the deformable object exerts pressure on the inlet openings. Using the geometry for providing blocking pressure on the inlet openings in the default state has the advantage that this mechanism is on the one hand cheap and simple to implement and on the other hand robust and reliable.

A further preferred embodiment is characterized in that the blocking assembly arranged such that the application of sufficient fluid pressure from an inlet channel of the at least two inlet channels to open that inlet channel causes an increase of closing pressure applied to at least one of the other inlet channels of the at least two inlet channels by the blocking assembly. Thus there is a mechanical link between those parts of the blocking assembly which close at least two inlet channels. This link is such that the fluid pressure from an inlet channel applied to the blocking assembly, which causes the blocking assembly to at least partially budge and open that inlet channel, is mechanically transmitted through the blocking assembly such that it increases the closing effect of the blocking assembly on at least one other inlet channel. Therefore, in the case of flow from an inlet channel into the central cavity and out of an outlet channel, the pressure with which the blocking assembly closes the other inlet channels is actually greater than in the state without any liquid flow from the inlet channels. Consequently, the presence of liquid flow from one inlet channel improves the blocking of the other inlet channels and the risk of contamination of the other reservoirs during operation of the injection device is further reduced.

In a further preferred embodiment, the blocking assembly comprises an element of adaptable shape of sufficient size to simultaneously close the at least two inlet channels. The element of adaptable shape may be so large that it only fits into the central cavity under strain. Thereby the pressure to expand of the element of adaptable shape causes a simultaneous blocking pressure on the inlet channels, even in the absence of fluid pressure from any of the inlet channels or outlet channels. The element of adaptable shape may be spherical in its default shape. The element of adaptable shape has sufficient elasticity to budge and open an inlet channel when sufficient liquid pressure is applied from that inlet channel. Using such an adaptable shape as blocking element has the advantage of providing a simple, robust and reliable solution for preventing reverse flow from the central cavity into any inlet channel.

In yet another preferred embodiment, the element of adaptable shape comprises a core material and an elastic surface material, wherein the elastic surface material is configured to deform on application of fluid pressure from an inlet channel of the at least two inlet channels such that that inlet channel is opened. In this embodiment the core material is harder and thus less elastic than the outer material. The hardness of the core material prevents the ball from being pressed inside any of the inlet or outlet channels, whereas the elastic outer material ensures a good sealing effect on the inlet channels, even in the presence of unevenness of the rim of the inlet openings. The combination of harder core material and elastic outer material combines the aforementioned respective advantages. The elasticity of the outer material is such that when fluid pressure in one of the inlet channels increases sufficiently, the elastic outer material buckles and thus opens the corresponding inlet channel. This fluid pressure causing the blocking element to open the respective inlet channel also presses the blocking element such that the blocking pressure on the other inlet channels is increased.

In a further preferred embodiment, the blocking assembly comprise a rubber seal for each inlet channel, wherein each rubber seal has a concave side facing the respective inlet channel and a convex side. Each rubber seal is cup-shaped. The rubber seals may consist of silicone rubber. Fluid pressure applied from the concave side is focused on the apex of the cup and can therefore act to open the valve at the apex point. Fluid pressure applied from the convex side, on the other hand, is distributed on the circumferential rim and sides of the cup and therefore does not act on a single point of the cup. In the arrangement with the concave side facing the inlet channel and the convex side facing the outlet channel, liquid pressure from the inlet channel causes the rubber seal to open and let the liquid pass, whereas liquid pressure from the outlet channel is blocked by the rubber seal. Thus such a cup-shaped rubber seal provides a check valve that is very simple in its construction and yet effective. It is also easily scaled to any number of inlet channels because only identical rubber seals need to be reproduced for each inlet channel.

In another preferred embodiment, each rubber seal comprises at least one slit configured to open and act as a liquid conduit from an inlet channel to one of the at least one outlet channels when fluid pressure is applied to the concave side and further configured to close and block liquid flow when fluid pressure is applied to the convex side. The at least one slit is situated at the apex of the rubber seal, which is cup-shaped. Consequently, the rubber seal expands at the apex when liquid pressure is applied from the concave side, thereby broadening the slit to a liquid conduit through which liquid can pass and further flow out of the outlet channel. Conversely, liquid pressure from the convex side acts primarily on the sides and the circumferential rim of the cup-shaped rubber seal, thereby acting to further compress the slit at the apex and to effectively prevent flow of fluids through the slit. Therefore, the rubber seal blocks liquid flow from the convex side, i.e. from the side facing the outlet channel. This embodiment presents a particularly simple, effective and also scalable implementation of a check valve by means of a rubber seal.

In a preferred embodiment, the blocking assembly comprises a blocking element for each inlet channel movable between a first position in which the respective inlet channel is closed and a second position in which the respective inlet channel is open. The blocking element may comprise elastic material and may also comprise rigid material. When the blocking element is in a position to close the inlet channel, liquid flow into the inlet channel is prevented. When the blocking element is in a position in which the inlet channel is open, a liquid may flow from the inlet channel into the central cavity and out of the outlet channel. The pressure of a liquid from an inlet channel on the blocking element of that inlet channel may act to move that blocking element from the closed position to the open position. The movement of the blocking element may be a translation movement, a rotation movement or any combination thereof. A certain part of the blocking element may be rigidly fixed. The movement of the blocking element may also comprise a contortion or deformation of the blocking element.

In a further preferred embodiment, the blocking assembly comprises a spring construction configured to provide the bias pressure. The spring construction may comprise spring means. The spring construction is arranged such that it exerts a force on the blocking assembly acting to press the blocking assembly against the respective inlet channel, thereby providing the bias pressure. Liquid pressure from the inlet channel on the blocking assembly needs to overcome this bias pressure in order to open the inlet channel by pushing the blocking element into the open position. When the liquid pressure from the inlet channel ceases, the spring construction acts to push the blocking assembly back into the position closing the inlet channel. Using a dedicated spring construction to provide the bias pressure permits a precise determination of the spring characteristics with which the bias pressure is applied.

In a further preferred embodiment, the spring construction comprises a spring for each blocking element. In this embodiment, each blocking element has an associated individual spring. This spring is connected to the blocking element at one end and may be connected to a wall of the central cavity at its other end. Using an individual spring for each blocking element permits applying a different maximum bias pressure and a different displacement-force characteristic curve for each blocking element, which may in particular be advantageous for the case that fluids with different convection properties flow through different inlet channels.

In yet a further preferred embodiment, the spring construction comprises at least one spring arranged between at least two blocking elements. The spring construction may also comprise at least one spring arranged between at least three or more blocking elements. The spring construction may comprise the minimum number of springs arranged between the blocking elements required to provide bias pressure to all blocking elements. Being arranged between at least two blocking elements means that the spring is connected with each of the blocking elements it is arranged between in such a way that, when one of the blocking elements is moved to open an inlet channel, the opening force applied to that blocking element is transmitted to the other associated blocking elements by the spring in question such that the pressure with which these other blocking elements are pressed against their respective inlet channels is increased. Therefore opening an inlet channel results in an improved closure of the other inlet channels with which the blocking element of the open inlet channel is connected via the spring. This embodiment provides the advantages that, firstly, a smaller number of springs is required than in the situation in which each blocking element has its own dedicated spring and that, secondly, opening an inlet channel by displacing the blocking element automatically results in an increased closing pressure on the blocking elements with which the blocking element of the opened inlet channel is connected via a spring. Therefore, there is reinforced protection against reverse flow into another inlet channel while a liquid is flowing from a first inlet channel into the central cavity and out of the outlet channel.

In a preferred embodiment, the blocking elements are ball-shaped. This means that the blocking elements are round and do not have edges. The blocking elements may be elastic such that they provide tight closure on the rims of the inlet channel, sealing those against the flow of liquid. Using ball-shaped blocking elements ensures that these are adapted to a wide variety of inlet channel geometries, thereby allowing cheap mass production.

In a further preferred embodiment, the blocking elements are flaps. The flaps may have the shape of a disc, a rectangular plate or that of some other flat object. The flaps are arranged to cover the inlet channel in the closed position. In the open position, the flaps may be displaced from the inlet channel through a displacement in a direction perpendicular to the inner surface of the central cavity, displacement in a direction parallel to the inner surface of the central cavity, by rotation or by bending. Flaps as blocking element have the advantage of providing good covering of the inlet channel without consuming a lot of volume in the central cavity.

In a preferred embodiment of the invention, the flaps are integrally formed with the valve body. This means that the flaps consist of the same material as the valve body and that they are directly connected to the valve body. In this embodiment, the flaps open the inlet channel by being bent by the liquid pressure from the inlet channel. Consequently, the fluid pressure from the inlet channel must overcome the bending stress of the flap in order to open that inlet channel. Further the bending stress of the flap acts as a spring force acting to push the flap back into the closed position. Therefore this embodiment has the advantage that no additional spring element aside from the flap itself is needed.

The invention is further directed at a medical device for delivering at least two drug agents from at least two separate reservoirs comprising an apparatus according to any of the aforementioned embodiments.

These as well as other advantages of various aspects of the present invention will become apparent to those of ordinary skill in the art by reading the following detailed description, with appropriate reference to the accompanying drawings:

DETAILED DESCRIPTION

Figure 1:
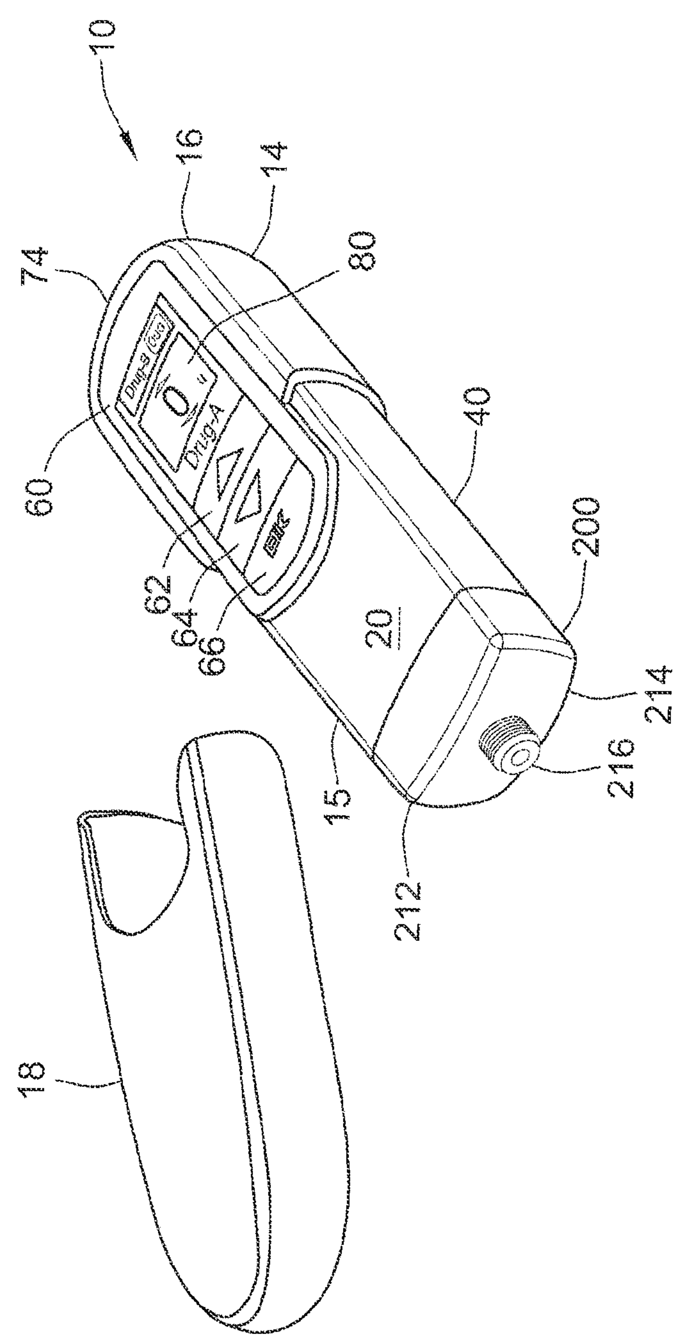
FIG. 1 illustrates a perspective view of the delivery device illustrated in FIGS. 1*a* and 1*b* with an end cap of the device removed.
Figure 2:
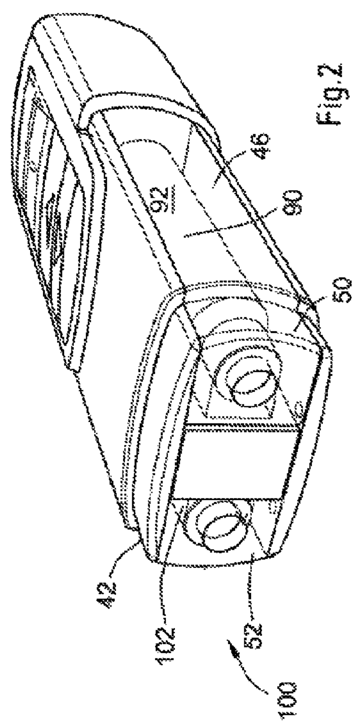
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 210 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
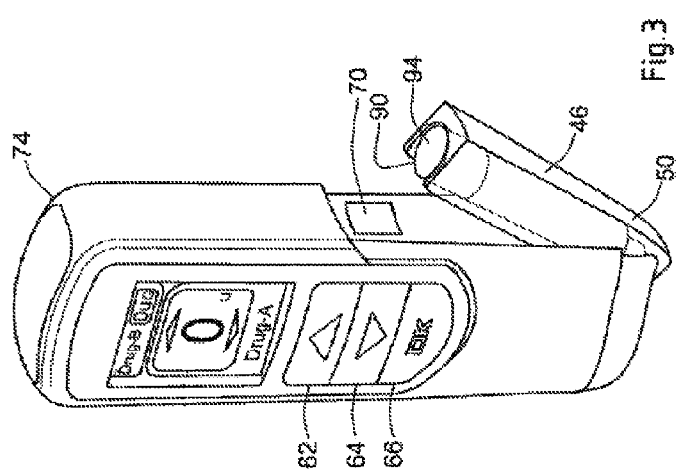
FIG. 3 illustrates a perspective view of the cartridge holder illustrated in FIG. 1 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
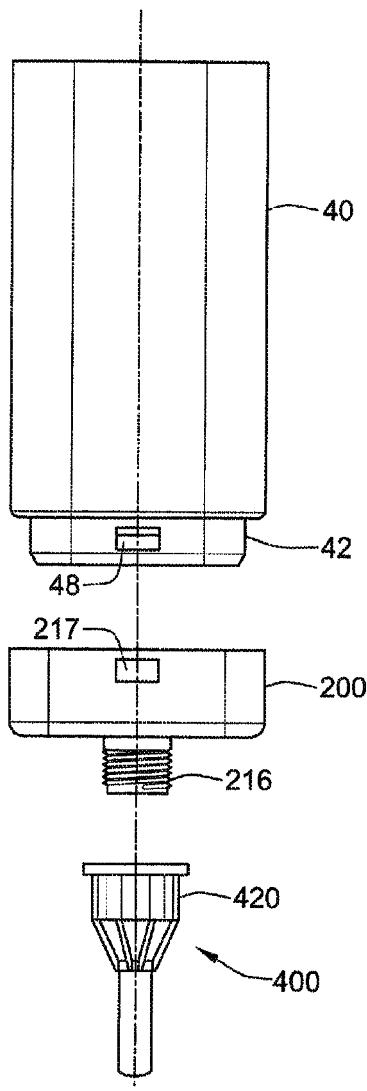
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
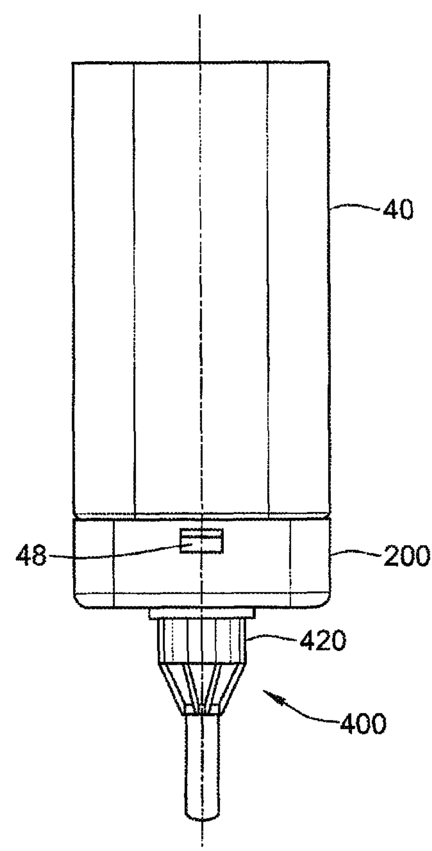
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
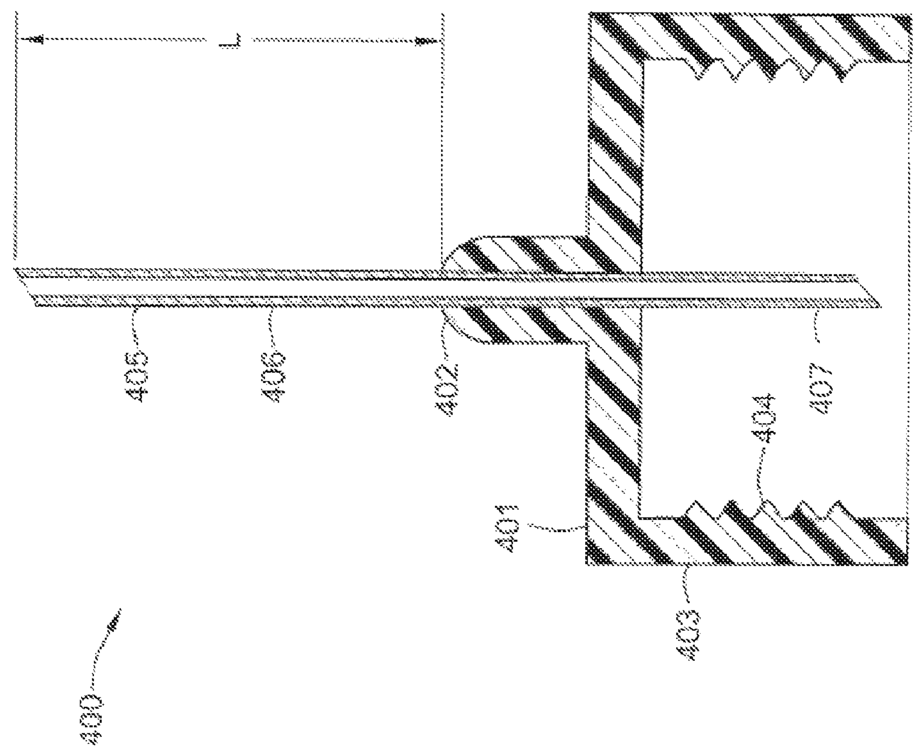
FIG. 6 illustrates one arrangement of the dose dispenser that may be mounted on a distal end of the delivery device.
Figure 7:
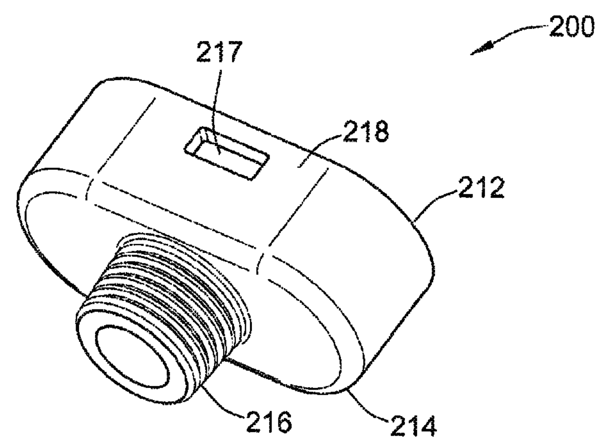
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 407 of the needle assembly 400 protrudes from an opposite side of the circular disc so that it is concentrically surrounded by the sleeve 403. In one needle assembly arrangement, the second or proximal piercing end 407 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
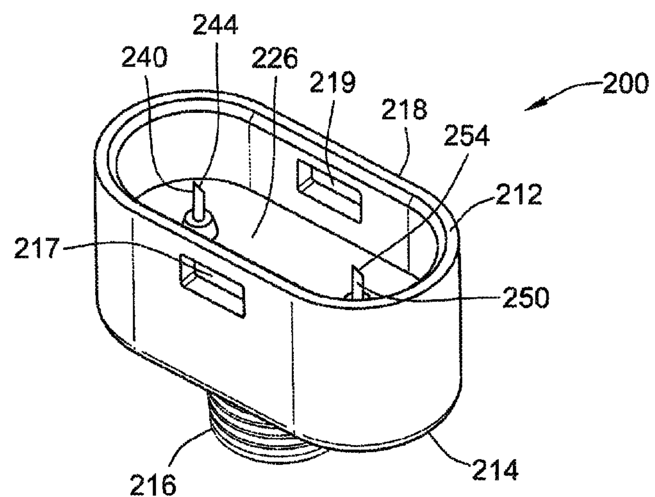
FIG. 8 illustrates another perspective view of the dispense interface illustrated in FIG. 4.
Figure 9:
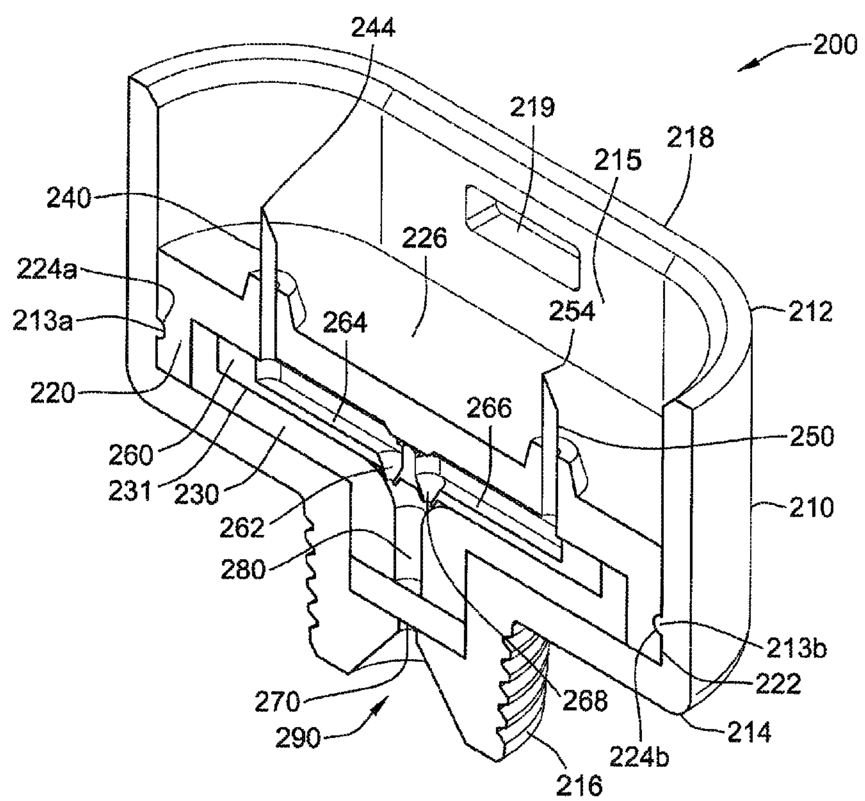
FIG. 9 illustrates a cross-sectional view of the dispense interface illustrated in FIG. 4.
Figure 10:
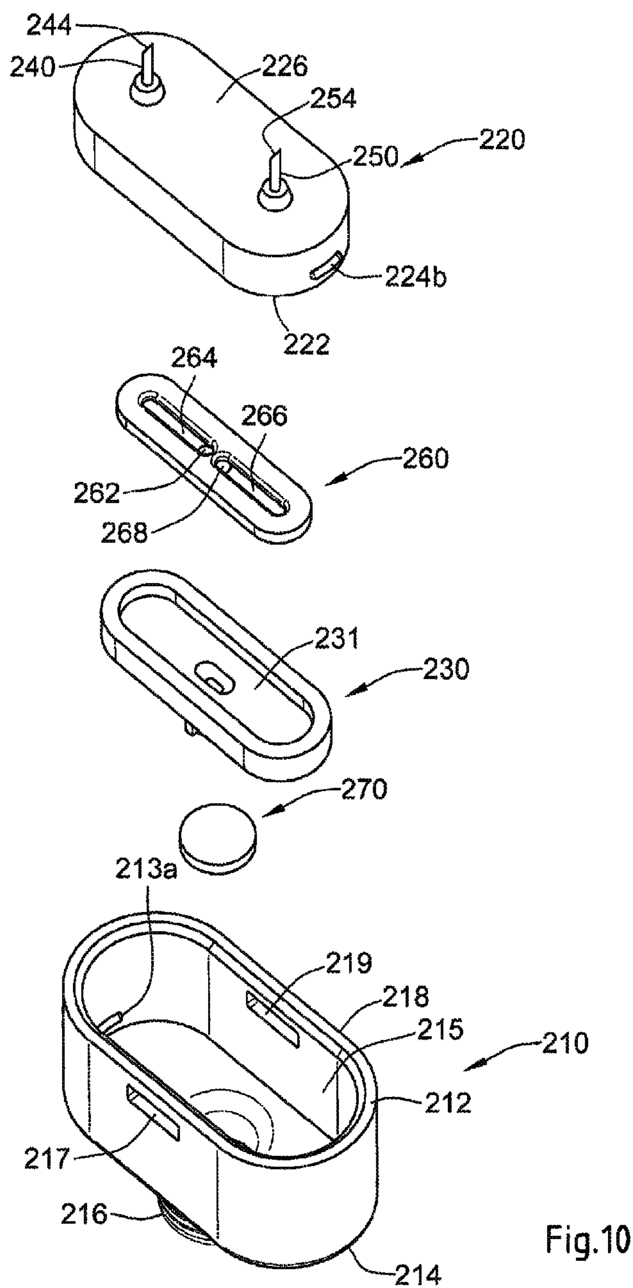
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
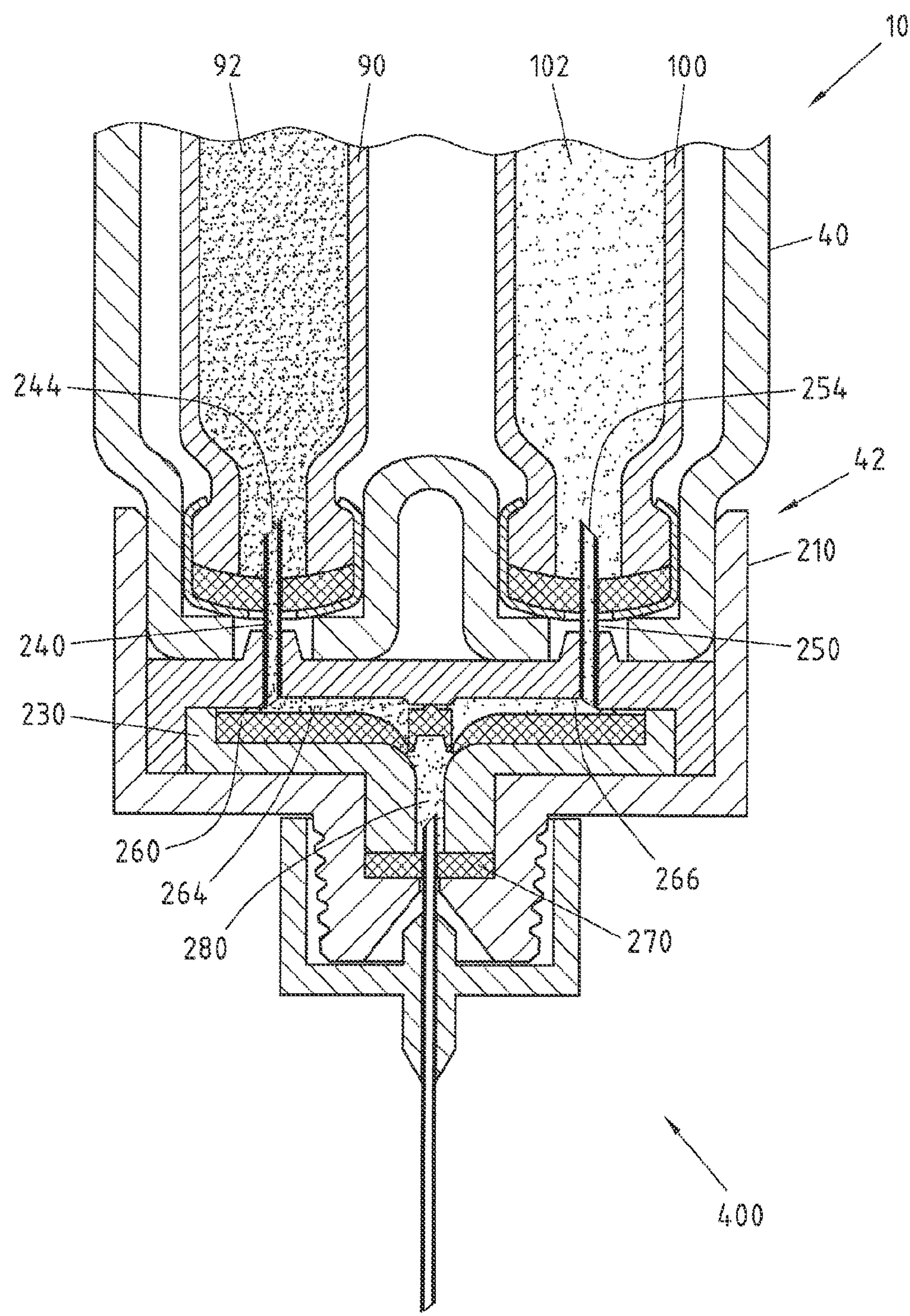
FIG. 11 illustrates a cross-sectional view of the dispense interface and dose dispenser mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

In the following embodiments of the present invention will be described in detail with reference to FIGS. 12 to 19*a* and 19*b*.

Figure 12:
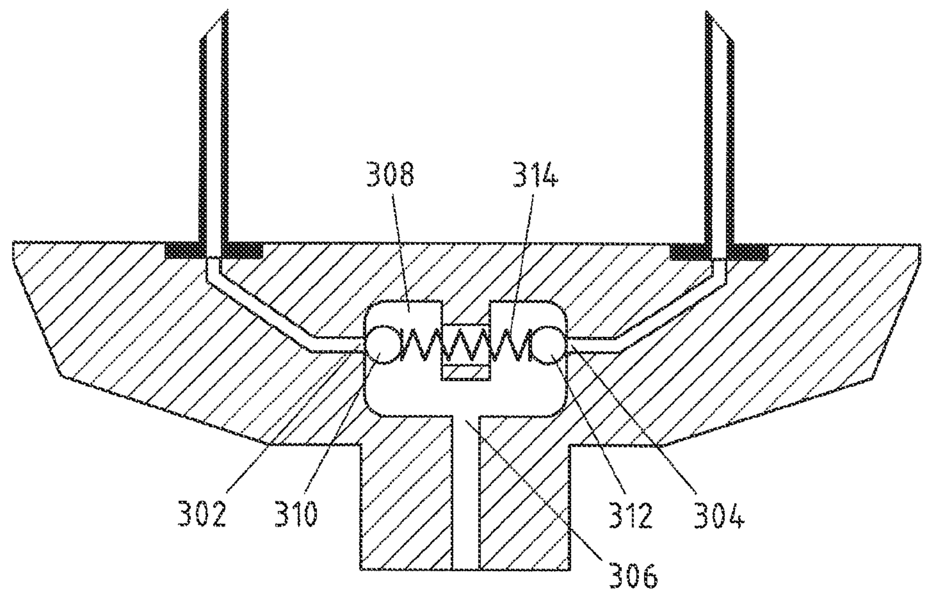
FIG. 12 illustrates a cross-sectional view of an embodiment of the valve body using ball-shaped blocking elements connected by a spring, which spring is arranged in a guidance opening.
Figure 13:
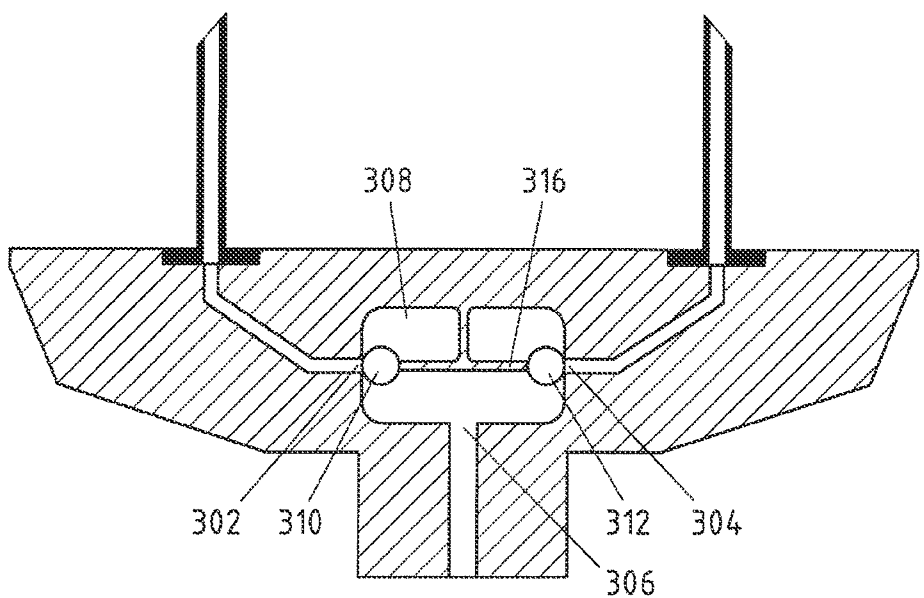
FIG. 13 illustrates a cross-sectional view of an embodiment of the valve body using ball-shaped blocking elements connected by a lever arm arrangement.

In FIGS. 12 and 13 cross-sectional views of an embodiment of the valve body are shown, comprising two inlet channels 302 and 304, one outlet channel 306 and a central cavity 308 connecting the inlet channels 302, 304 and the outlet channel 306. A first ball-shaped blocking element 310 and a second ball-shaped blocking element 312 are contained within the central cavity 308 and connected by a spring 314. The spring 314 is arranged in a guidance opening formed integrally with the valve body. The ball-shaped blocking elements 310, 312 and the spring 314 are arranged such that in the absence of outside pressure, the spring provides a bias pressure to press the first ball-shaped blocking element 310 against the first inlet channel 302 and the second ball-shaped blocking element 312 against the second inlet channel 304 respectively, thereby closing both inlet channels 302, 304.

The inlet channels 302 and 304 are in fluid communication with a first reservoir and with a second reservoir (generally shown for example in FIG. 11 as reservoirs 90 and 100). Moreover, outlet channel 306 is configured for fluid connection with a septum 270, which has been also discussed with reference to FIG. 11.

The functionality of the valve is as follows: when a liquid from the first reservoir, for example a drug component, is to be passed through the valve, for example as the first part of an injection procedure for the sequential injection of two different drug components, the liquid enters the first inlet channel 302 from the reservoir. As the liquid enters the first inlet channel 302, the pressure therein increases until it suffices to push the first ball-shaped blocking element 310 away from the first inlet channel 302 against the pressure applied to the first ball-shaped blocking element 310. Now the liquid can enter the central cavity 308 and flow outwards through the outlet channel 306. The liquid cannot enter the second inlet channel 304, because the second ball-shaped blocking element 312 is pressed against the second inlet channel 304 by the spring 314, thereby closing the second inlet channel 304 from liquid flow. The closing pressure applied by the spring 314 on the second ball-shaped blocking element 312 is a combination of the bias pressure with which the spring presses the second ball-shaped blocking element 312 against the second inlet channel 304 in the equilibrium state and the force with which the first ball-shaped blocking element 310 is pushed in the open position, because this force is transmitted at least in part to the second ball-shaped blocking element 312 by the spring 314.

Even if the liquid is prevented from flowing out of the outlet channel 306, for example because of an obstruction in a needle fluidly connected to the outlet channel 306, there is no reverse flow in the second inlet channel 304. This is for the following reasons: As long as liquid flows from the first inlet channel 302 into the central cavity 308, a force sufficient to open the first inlet channel 302 acts on the first ball-shaped blocking element 310 and this force is added at least in part to the force with which the second ball-shaped blocking element 312 is pressed against the second inlet channel 304, thereby closing the second inlet channel 304. But even if the liquid flow from the first inlet channel 302 stops and the first ball-shaped blocking element 310 returns to a position blocking the first inlet channel 302 because of the restored pressure equilibrium, there is always at the very least the bias pressure applied by the spring 314 acting on the second ball-shaped blocking element 312 to block the second inlet channel 304. Therefore reverse flow from the central cavity 308 into the second inlet channel 304 is prevented.

Due to its symmetry with respect to the first inlet channel 302 and the second inlet channel 304, the valve functions according to the analogous principle as just described when liquid from the second reservoir, such as a second drug component for the second part of the injection procedure, passes through the central cavity 308 and further out of the outlet channel 306, with the first and second ball-shaped blocking elements 310, 312 and first and second inlet channels 302, 304, respectively, switching their roles.

In the valve body illustrated in FIG. 13, the first ball-shaped blocking element 310 and the second ball-shaped blocking element 312 are connected to the valve body by an approximately T-shaped lever arm arrangement 316 made of plastic material. The base of the lever arm arrangement 316 is integrally connected to the valve body whereas the end of each arm of the lever arm arrangement 316 is connected to the first ball-shaped blocking element 310 or the second ball-shaped blocking element 312, respectively. The lever arm arrangement 316 is constructed such that already in the equilibrium state, i.e. in the absence of fluid pressure, strain in the lever arm arrangement 316 acts to exert a bias force on the ball-shaped blocking elements 310, 312, pressing them against the first and second inlet channel 302 and 304, respectively, such that both inlet channels 302, 304 are closed. The lever arm arrangement 316 is further configured such that the force required for a displacement of the first ball-shaped blocking element 310, as occurs when the first inlet channel 302 is opened through fluid pressure from within the first inlet channel 302, is at least partially transmitted to the second ball-shaped blocking element 312 by the lever arm arrangement 316 such that the force with which the second ball-shaped blocking element 312 is pressed against the second inlet channel 304 is increased. Because of symmetry, the same effect occurs in the opposite direction when the second ball-shaped blocking element 312 is displaced. Therefore the lever arm arrangement 316 corresponds in its mechanical effect to the spring 314 of FIG. 12.

Figure 14:
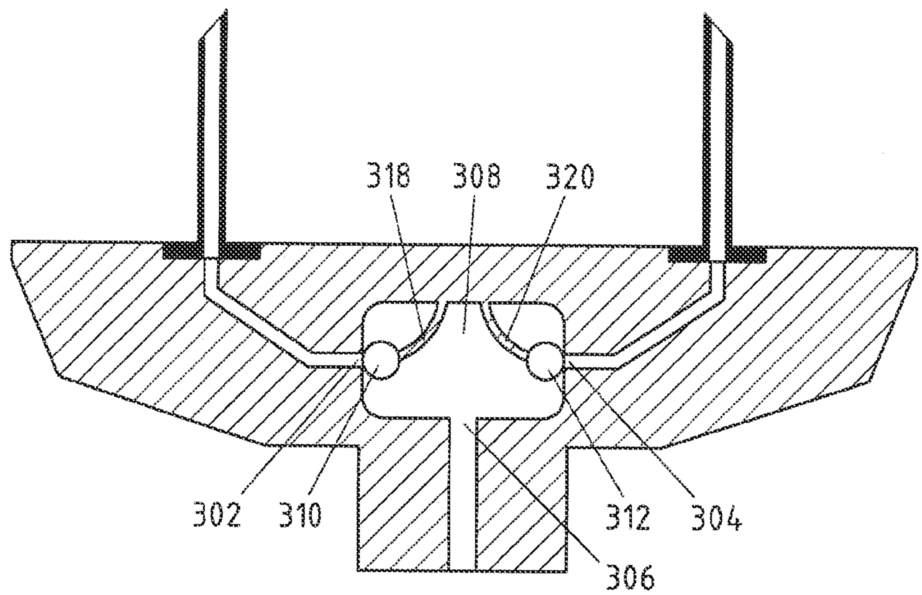
FIG. 14 illustrates a cross-sectional view of an embodiment of the valve body using ball-shaped blocking elements each having their own dedicated curved lever arm.

FIG. 14 illustrates the cross-section of a further embodiment of a valve body. This valve body corresponds to that of FIG. 13 with the difference that instead of a single approximately T-shaped lever arm arrangement 316 the valve body comprises a first and second curved lever arm 318, 320 made of plastic material and separately connecting the first and second ball-shaped blocking elements 310, 312 to the valve body. The curved lever arms 318, 320 are constructed such that they are strained to provide a bias force pressing the first and second ball-shaped blocking elements 310, 312 against the first and second inlet channels 302, 304, respectively.

Likewise, displacement of a ball-shaped blocking elements 310, 312 further strains the associated curved lever arm 318, 320, thereby resulting in a resetting force greater than the bias force acting on the displaced ball-shaped blocking element 310, 312 toward a closing position of the respective inlet channel 302, 304. Because of the lack of a direct mechanical connection in the embodiment of FIG. 14—unlike the embodiments of FIG. 12 and FIG. 13—the displacement force on any ball-shaped blocking element 310, 312 is not directly transmitted to the respective other ball-shaped blocking element 310, 312.

Figure 15:
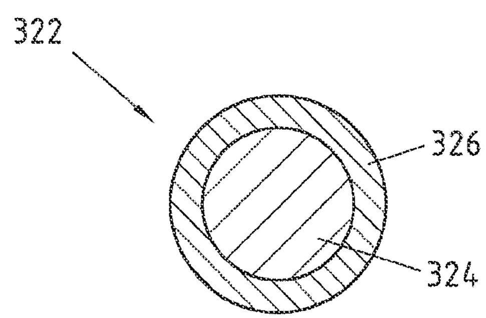
FIG. 15 illustrates a spherical element usable as blocking assembly.

FIG. 15 illustrates a spherical element 322 consisting of a core material 324 and an outer material 326, wherein the core material 324 is more rigid than the elastic outer material 326. The elasticity of the outer material 326 makes the shape of the spherical element 322 adaptable.

Figure 16:
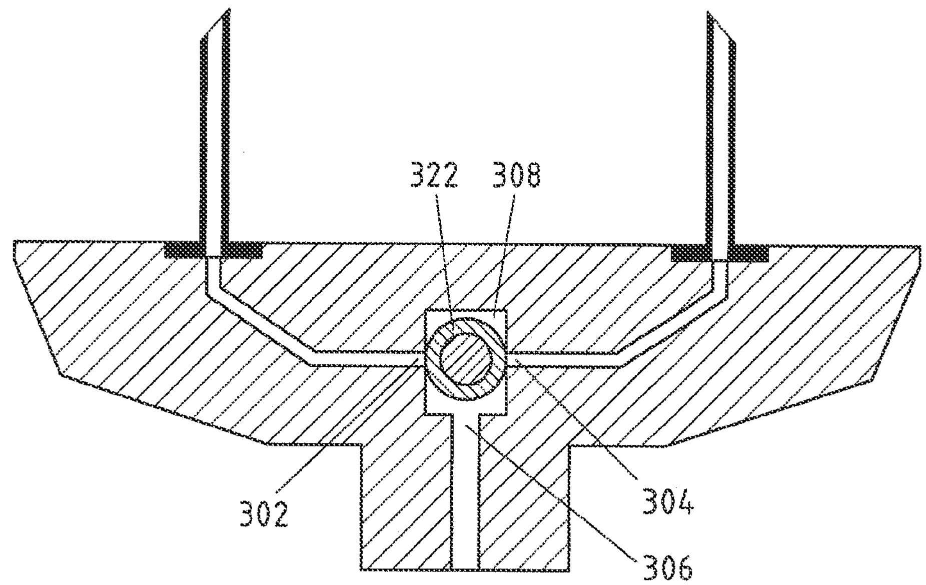
FIG. 16 illustrates a cross-sectional view of an embodiment of the valve body with the spherical element of FIG. 15 used as blocking assembly.

FIG. 16 illustrates a valve body comprising a central cavity 308, first and second inlet channels 302, 304 and an outlet channel 306 as in the embodiments illustrated in FIGS. 12 to 14. The other external structures and connections of this valve body are also identical to those of FIGS. 12 to 14.

Inside the central cavity 308, there is a spherical element 322 as illustrated in FIG. 15. The spherical element 322 is dimensioned such that it is under strain to expand when fit inside the central cavity 308. In particular, this constriction of the spherical element 322 results in a deformation and corresponding strain of the elastic outer material 326. Consequently, in an equilibrium state in the absence of any fluid pressure, the spherical element 322 closes the inlet channels 302, 304 and exerts bias pressure on the inlet channels 302, 304, thereby ensuring that any unevenness of the rim of the inlet channels 302 and 304 is well sealed. On the other hand, the rigid core material 324 prevents the ball from being pressed inside any inlet channel 302, 304 or the outlet channel 306. Optionally, there may be recesses in the valve body around the openings of the inlet channels 302, 304 in order to hold the spherical element 322 in place.

The functionality of the valve is similar to that illustrated in FIG. 12 and described as follows. When a liquid from the first reservoir, for example a drug component, is to be passed through the valve, for example as the first part of an injection procedure for the sequential injection of two different drug components, the liquid enters the first inlet channel 302 from the reservoir. As the liquid enters the first inlet channel 302, the pressure therein increases until it suffices to counteract the bias pressure acting on the first inlet channel 302 and deform the elastic outer material 326 sufficiently to form a fluid passageway from the first inlet channel to the outlet channel 306. Now the liquid can enter the central cavity 308 and flow outwards through the outlet channel 306. The liquid cannot enter the second inlet channel 304, because the spherical element 322 remains pressed against the second inlet channel 304 by virtue of its strain to expand, thereby closing the second inlet channel 304 from liquid flow. The closing pressure applied by the spherical element 322 on the second inlet channel 304 is a combination of the bias pressure with which the spherical element 322 presses against the second inlet channel 304 in the equilibrium state and the additional pressure with which the elastic outer material 326 is deformed at the first inlet channel 302. This force is transmitted at least in part to the second inlet channel 304 by the spherical element 322.

Even if the liquid is prevented from flowing out of the outlet channel 306, for example because of an obstruction in a needle fluidly connected to the outlet channel 306, there is no reverse flow in the second inlet channel 304. This is for the following reasons: As long as liquid flows from the first inlet channel 302 into the central cavity 308, a force sufficient to open the first inlet channel 302 acts on the spherical element 322 and this force is added at least in part to the force with which the spherical element 322 is pressed against the second inlet channel 304, thereby closing the second inlet channel 304. But even if the liquid flow from the first inlet channel 302 stops and the elastic outer material 326 expands again to close the first inlet channel 302, there is always at the very least the bias pressure applied by the spherical element 322 acting to block the second inlet channel 304. Therefore reverse flow from the central cavity 308 into the second inlet channel 304 is prevented.

Due to its symmetry with respect to the first inlet channel 302 and the second inlet channel 304, the valve functions according to the analogous principle as just described when liquid from the second reservoir, such as a second drug component for the second part of the injection procedure, passes through the central cavity 308 and further out of the outlet channel 306.

Figure 17:
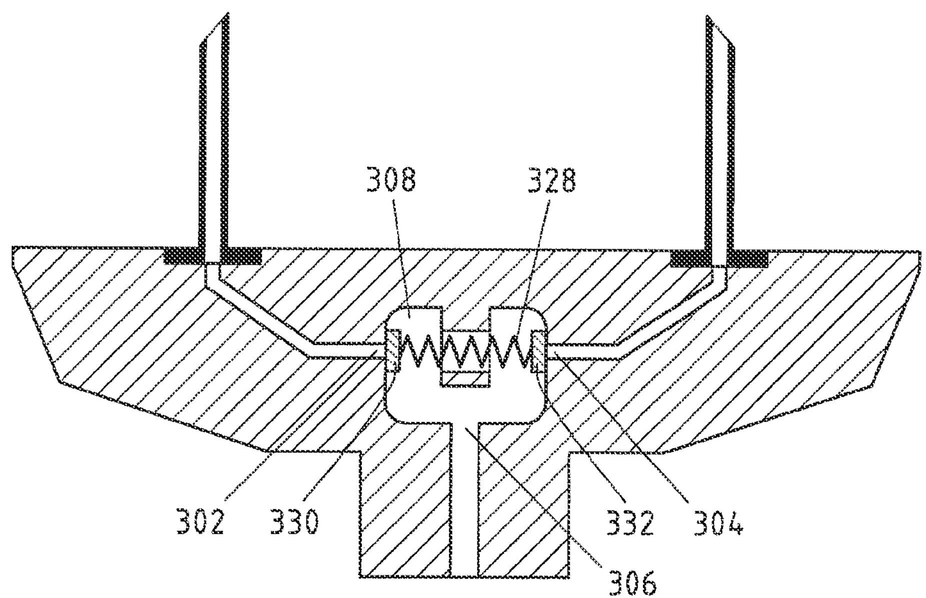
FIG. 17 illustrates a cross-sectional view of an embodiment of the valve body using flaps connected by a spring, which spring is arranged in a guidance opening.

FIG. 17 shows the cross-section of a further embodiment of a valve body. This embodiment is identical to that of FIG. 12 except for the fact that instead of ball-shaped blocking elements 310, 312, a first flap 330 and a second flap 332 is used for blocking the first inlet channel 302 and second inlet channel 304, respectively. The method of operation of this embodiment is the same as that of FIG. 12.

Figure 18:
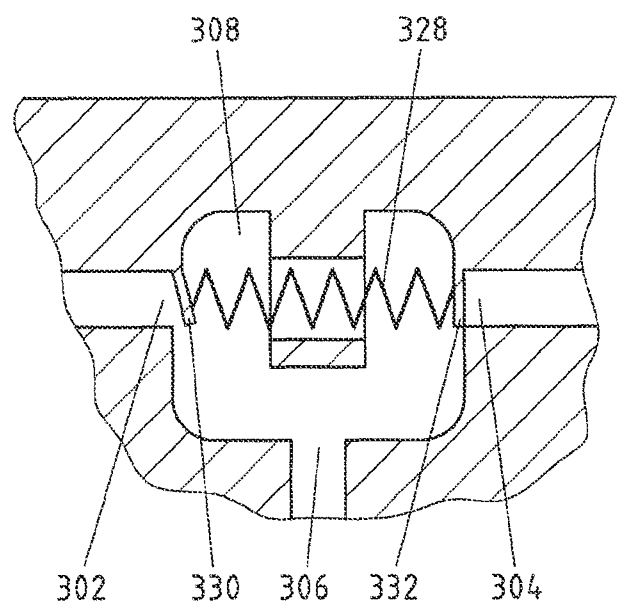
FIG. 18 illustrates a cross-sectional view of an embodiment of the valve body as in FIG. 17 in which the flaps are formed integrally with the valve body.

FIG. 18 shows a variation of the embodiment of FIG. 17 in which the flaps 330, 332 are formed integrally with the valve body. While the principle of operation of this embodiment is identical to that of the embodiment of FIG. 17, because of the integral connection between the flaps 330, 332 and the valve body, the opening of the inlet channels 302, 304 does not involve a translational movement of the respective flap 330, 332, but rather a bending of the respective flap 330, 332. Therefore in order to open the appropriate inlet channel 302, 304, the fluid pressure must not only overcome the bias pressure of the spring 328 acting on the flap 330, 332, but also the internal strain of the flap 330, 332 being bent. Consequently, the resistive force of this bending acts as a restoring force to returning the flap 330, 332 to their respective closed position in addition to the force applied by the spring 328.

Figure 19A:
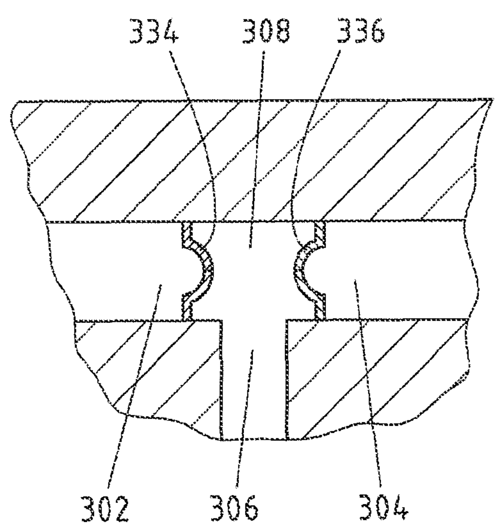
FIGS. 19*a* and 19*b* illustrate a cross-sectional view of an embodiment of the valve body using cup-shaped blocking elements.
Figure 19B:
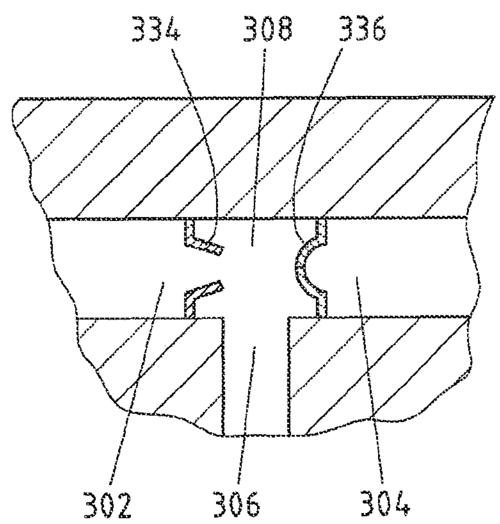

FIG. 19*a* and FIG. 19*b* illustrate a further embodiment of the valve body. In this embodiment, the central cavity 308 is just formed by the T-shaped intersection of the inlet channels 302, 304 and the outlet channel 306. The further external fluid connections of the inlet channels 302, 304 and the outlet channel 306 as well as the intended mode of operation of this valve body is identical to that of the other embodiments.

This embodiment comprises cup-shaped rubber seals 334, 336 between each inlet channel 302, 304 and the central cavity 308. The concave side of the rubber seals 334, 336 faces the corresponding inlet channel 302, 304 and the convex side of the rubber seals 334, 336 faces the central cavity 308 and consequently also the outlet channel 306. Each rubber seal 334, 336 comprises a slit at its apex, corresponding to the apex of the cup-shape.

In the equilibrium state depicted in FIG. 19*a*, i.e. in the absence of external pressure, the cup-shape of the rubber seals 334, 336 is closed, thereby preventing liquid flow through the slits of the rubber seals 334, 336.

The shape and construction of the rubber seals 334, 336 ensures that liquid pressure from the concave side focuses on the apex of the rubber seal 334, 336, thereby causing the rubber seal 334, 336 to open at its slit and allow liquid flow from the concave side to the convex side. FIG. 19*b* shows the first rubber seal 334 in this open state and the second rubber seal 336 in the closed state.

Once the liquid pressure from the concave side subsides, the rubber seal 334, 336 resumes its closed arrangement through its internal torsion forces as depicted in FIG. 19*a*.

On the other hand, any liquid pressure from the convex side of a rubber seal 334, 336 is distributed on the lateral side of the cup-shape and the rim of the rubber seals 334, 336, thereby acting to further compress the slit in the apex and therefore close the respective rubber seal 334, 336 even tighter.

Because of these mechanical properties of the rubber seals 334, 336, the rubber seals enable liquid flow from any of the inlet channels 302, 304 through the central cavity 308 and out of the outlet channel 306 in the presence of liquid pressure from that inlet channel 302, 304, but effectively prevent any reverse flow into any other inlet channel 302, 304.

An example for the operation of this arrangement is given in the following. At the onset, both rubber seals 334, 336 are closed as shown in FIG. 19*a*. When a liquid from the first reservoir, for example a drug component, is to be passed through the valve, for example as the first part of an injection procedure for the sequential injection of two different drug components, the liquid enters the first inlet channel 302 from the reservoir. As the liquid enters the first inlet channel 302, the pressure therein increases until it suffices to open the first rubber seal 334 as shown in FIG. 19*b*. Now the liquid can enter the central cavity 308 and flow outwards through the outlet channel 306. The liquid cannot enter the second inlet channel 304, because the second rubber seal 336 is closed and is actually shut tighter because of the liquid pressure acting from the central cavity 308 and therefore on the convex side of the rubber seal 336.

Even if the liquid is prevented from flowing out of the outlet channel 306, for example because of an obstruction in a needle fluidly connected to the outlet channel 306, there is no reverse flow into the second inlet channel 304. This is because an obstruction in the outlet channel 306 will cause an increase in the pressure on the convex side of the second rubber seal 336, thereby making the closure of the second inlet channel 304 ever tighter. Therefore reverse flow from the central cavity 308 into the second inlet channel 304 is prevented.

Due to its symmetry with respect to the first inlet channel 302 and the second inlet channel 304, the rubber seals 334, 336 function according to the analogous principle as just described when liquid from the second reservoir, such as a second drug component for the second part of the injection procedure, passes through the central cavity 308 and further out of the outlet channel 306, with the first and second rubber seals 334, 336 and first and second inlet channels 302, 304, respectively, switching their roles.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyhepta-decanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4 (1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus comprising:

a valve body comprising at least two inlet channels and at least one outlet channel and forming a central cavity connecting the at least two inlet channels and the at least one outlet channel, a blocking assembly comprising a spherical element of adaptable shape positioned within the central cavity such that the spherical element closes the at least two inlet channels at the same time;

wherein the blocking assembly is arranged such that the at least two inlet channels are both closed by default and for opening at least one of the at least two inlet channels when fluid pressure is applied from that inlet channel;

wherein each of the at least two inlet channels is configured for fluid communication with a respective reservoir of at least two reservoirs.

2. The apparatus of claim 1, wherein the blocking assembly is configured to apply bias pressure on the at least two inlet channels.

3. The apparatus of claim 1, wherein the blocking assembly is arranged such that the application of sufficient fluid pressure from an inlet channel of the at least two inlet channels to open that inlet channel causes an increase of closing pressure applied to at least one of the other inlet channels of the at least two inlet channels by the blocking assembly.

4. The apparatus of claim 3, wherein the element of adaptable shape comprises a core material and an elastic surface material, wherein the elastic surface material is configured to deform on application of fluid pressure from an inlet channel of the at least two inlet channels such that that inlet channel is opened.

5. A medical device for delivering at least two drug agents from the at least two reservoirs comprising of the apparatus according to claim 1.

* * * * *